(12) United States Patent
Kroll

(10) Patent No.: US 7,447,544 B1
(45) Date of Patent: *Nov. 4, 2008

(54) SYSTEM AND METHOD FOR CONTROLLING THE RECORDING OF DIAGNOSTIC MEDICAL DATA IN AN IMPLANTABLE MEDICAL DEVICE

(75) Inventor: Mark W. Kroll, Crystal Bay, MN (US)

(73) Assignee: Pacesetter, Inc., Sylmar, CA (US)

( * ) Notice: Subject to any disclaimer, the term of this patent is extended or adjusted under 35 U.S.C. 154(b) by 512 days.

This patent is subject to a terminal disclaimer.

(21) Appl. No.: 10/782,123

(22) Filed: Feb. 18, 2004

(51) Int. Cl.
*A61N 1/37* (2006.01)
(52) U.S. Cl. .......................... 607/9; 600/508
(58) Field of Classification Search ................ 600/509, 600/523, 508; 607/9
See application file for complete search history.

(56) References Cited

U.S. PATENT DOCUMENTS

| | | | | |
|---|---|---|---|---|
| 5,431,691 A | | 7/1995 | Snell et al. ................... 607/27 |
| 5,522,850 A | * | 6/1996 | Yomtov et al. ................. 607/5 |
| 5,732,708 A | | 3/1998 | Nau et al. .................... 600/523 |
| 5,782,885 A | | 7/1998 | Andersson ................... 607/17 |
| 5,785,660 A | * | 7/1998 | van Lake et al. ............ 600/523 |
| 5,891,178 A | | 4/1999 | Mann et al. .................... 607/27 |
| 5,908,392 A | * | 6/1999 | Wilson et al. ............... 600/509 |
| 5,941,831 A | | 8/1999 | Turcott ....................... 600/515 |
| 6,035,233 A | | 3/2000 | Schroeppel et al. ......... 600/515 |
| 6,115,627 A | | 9/2000 | Street ........................ 600/515 |
| 6,272,377 B1 | | 8/2001 | Sweeney et al. ............. 600/515 |
| 6,275,734 B1 | | 8/2001 | McClure et al. .............. 607/27 |
| 6,304,773 B1 | | 10/2001 | Taylor et al. ................ 600/515 |
| 6,308,094 B1 | | 10/2001 | Shusterman et al. ......... 600/516 |
| 6,400,982 B2 | | 6/2002 | Sweeney et al. ............. 600/515 |
| 6,445,949 B1 | | 9/2002 | Kroll ............................. 607/4 |
| 6,516,219 B1 | | 2/2003 | Street ........................ 600/515 |
| 6,519,493 B1 | | 2/2003 | Florio et al. .................... 607/9 |
| 6,594,523 B1 | | 7/2003 | Levine ......................... 607/30 |
| 6,719,701 B2 | | 4/2004 | Lade | |
| 2002/0147409 A1 | | 10/2002 | Baker et al. | |
| 2003/0088289 A1 | | 5/2003 | Levine et al. ................ 607/30 |
| 2003/0144595 A1 | * | 7/2003 | Lade .......................... 600/485 |

OTHER PUBLICATIONS

NonFinal Office Action, mailed Sep. 13, 2006: Related U.S. Appl. No. 10/782,684.
Final Office Action, mailed Mar. 6, 2007: Related U.S. Appl. No. 10/782,684.
Advisory Action, mailed May 15, 2007: Related U.S. Appl. No. 10/782,684.

(Continued)

*Primary Examiner*—Mark W Bockelman
*Assistant Examiner*—Eric D Bertram

(57) ABSTRACT

Techniques are provided for controlling the recording of diagnostic data, such as intracardiac electrogram (IEGM) data, so as to reduce device power consumption. In one technique, the risk of onset of an arrhythmia is evaluated and the recording of diagnostic data is then selectively controlled based upon the evaluation. More specifically, a temporary "pre-trigger" memory for recording IEGM data is activated only at times when there is a significant risk that an arrhythmia will actually occur. Power savings are thereby achieved as compared to devices that require the pre-trigger memory to be continuously active. In another technique, parameters employed to trigger the recording of diagnostic data are adaptively modified to reduce the likelihood of any unnecessary recording of such data. Preferably, both the risk-based techniques and the adaptive techniques are implemented in the same system.

23 Claims, 10 Drawing Sheets

OTHER PUBLICATIONS

NonFinal Office Action, mailed Aug. 6, 2007: Related U.S. Appl. No. 10/782,684.
Final Office Action, mailed Jan. 31, 2008: Related U.S. Appl. No. 10/782,684.
NonFinal Office Action, mailed Nov. 5, 2007: Related U.S. Appl. No. 10/782,684.
NonFinal Office Action, mailed Mar. 11, 2008: Related U.S. Appl. No. 10/782,684.

* cited by examiner

SYSTEM AND METHOD FOR CONTROLLING THE RECORDING OF DIAGNOSTIC MEDICAL DATA IN AN IMPLANTABLE MEDICAL DEVICE

CROSS REFERENCE TO RELATED APPLICATIONS

This application is related to copending U.S. patent application Ser. No. 10/782,684, titled "System and Method for Controlling the Recording of Diagnostic Medical Data in an Implantable Medical Device", filed Feb. 18, 2004.

FIELD OF THE INVENTION

The invention relates generally to implantable medical devices such as pacemakers and implantable cardioverter defibrillators (ICDs) and in particular to techniques for controlling the recording of intracardiac electrograms (IEGMs) therein.

BACKGROUND

Implantable medical devices are often configured to be used in conjunction with an external programmer that allows a physician to display information detected by the implanted device. For example, the external programmer may operate to display electrical cardiac signals detected by the implantable device in the form of IEGMs. An IEGM is a graphic depiction of electrical signals emitted by active cardiac tissue as detected by electrodes placed in the heart. The electrical signals are digitized and recorded with the implanted device along with an indication of the date and time, and ultimately transmitted to the external programmer for display thereon, typically during follow-up sessions with the physician sometime after the device has been implanted. Alternatively, the implanted device is controlled to transmit the IEGM signals in real-time during the follow-up session. The external programmer may also be configured to receive real-time surface electrocardiogram (ECG) signals from an external ECG detector, for display along with contemporaneous real-time IEGM signals transmitted from the implanted device.

The implanted device may also be configured to detect various events, such as paced and sensed events or premature atrial contractions (PACs), and to generate event codes representative of the events for transmission to the external programmer. The events are detected and event codes are stored in the implanted device along with the corresponding IEGM signals for subsequent transmission to the external programmer or are detected and transmitted to the external programmer in real-time along with contemporaneous IEGM signals. The external programmer generates event marker icons based on the event code and displays the icons along with the IEGM signals and surface ECG signals. Exemplary event markers are: "P" for a sensed event in the atria; "R" for a sensed event in the ventricles; "A" for a paced event in the atria, and "V" for a paced event in the ventricles. Along with the event markers, the programmer may also display variable length horizontal lines representative of the length of atrial and ventricular refractory periods associated with certain events, as well as numerical values indicative of heart rate and indicative of various measured intervals between atrial and ventricular events, based on still further information recorded and transmitted by the implantable device.

Such displays of IEGMs and event markers are helpful in permitting the physician to diagnose arrhythmias and to program the implanted device to provide optimal therapy. U.S. Pat. No. 5,431,691 to Snell et al. entitled "Method and System for Recording and Displaying a Sequential Series of Pacing Events" provides a description of the operation of an exemplary pacemaker and external programmer including a detailed description of the generation, transmission and display of IEGM data and event markers. U.S. Pat. No. 5,431,691 to Snell et al. is incorporated by reference herein.

Given the memory space limitations and power limitations within implantable medical devices, it is desirable to detect and record IEGMs and corresponding event markers only during periods of interest, such as during an arrhythmia. Accordingly, some implantable devices are configured to begin recording IEGM and other diagnostic data only upon detection of an actual arrhythmia. Although this technique is helpful in reducing power and memory consumption, by activating the recording of diagnostic data only upon detection of arrhythmia, the device therefore does not record diagnostic data leading to the onset of the arrhythmia, which is often of particular interest to the physician. In this regard, it is often desirable to program the implanted device so as to deliver therapy to prevent the onset of an arrhythmia, rather than to merely respond to an arrhythmia once one has already occurred. IEGM and other diagnostic data recorded prior to the onset of arrhythmia is very helpful as it allows the physician to review the circumstances leading to the arrhythmia so that preventative therapies may be adjusted as needed to achieve optimal effectiveness.

To remedy this problem, certain implantable devices are configured to allow so-called "pre-trigger data" to be saved along with data recorded during an arrhythmia. Briefly, the device continuously detects and records diagnostic data in a circular first-in/first-out (FIFO) queue. If an arrhythmia is detected, the diagnostic data recorded just prior to the onset of the arrhythmia is transferred from the FIFO queue to long-term memory, so that it can be saved along with data recorded during the actual arrhythmia for subsequent review by the physician. In this manner, diagnostic data detected during the period of time leading to the onset of the arrhythmia is saved in long-term memory for subsequent review by the physician, without requiring that all diagnostic data be saved in long-term memory at all times. Hence, the term "pre-trigger data" refers to diagnostic data that is temporarily recorded prior to the detection of an event triggering long-term recordation of diagnostic data. An example of a pre-trigger technique and is set forth in U.S. Pat. No. 5,732,708 to Nau et al., entitled "Method for Storing EGM and Diagnostic Data in a Read/Write Memory of an Implantable Cardiac Therapy Device."

Although pre-trigger recording techniques represent a significant improvement over techniques that fail to save data occurring prior to the onset of an arrhythmia, disadvantages remain. In particular, pre-trigger techniques require that the pre-trigger memory be active at all times, which results in a considerable drain on the power supply of the implanted device. Indeed, for state-of-the-art devices, the need to continuously record diagnostic data in pre-trigger memory can result in the loss of six months of device longevity. Accordingly, it would be highly desirable to provide techniques that allow for saving pre-arrhythmia or other pre-trigger diagnostic data for subsequent review but which do not require that the pre-trigger memory be continuously active. It is to this end that the present invention is primarily directed.

SUMMARY

In accordance with a first aspect, techniques are provided for controlling the recording of diagnostic data such as IEGM data within an implantable medical device, which provide for the recording of pre-arrhythmia data but which do not require that diagnostic data be continuously recorded within a temporary "pre-trigger" memory. Briefly, the device evaluates the likelihood that circumstances will arise wherein diagnostic medical data is to be recorded and then selectively controls the recording of diagnostic data based upon such as evaluation. In other words, the recording of diagnostic data is controlled based on a risk-based analysis. In one example, the device evaluates whether there is an elevated risk of an arrhythmia by, for example, monitoring heart rate variability, then activates a pre-trigger memory for temporarily recording diagnostic data during the period of elevated risk. If an arrhythmia occurs, diagnostic data recorded in the pre-trigger memory prior to the arrhythmia, as well as data recorded during the arrhythmia, are transferred to long-term memory for subsequent review by a physician. In another example, the device predicts the onset of an imminent arrhythmia by, for example, monitoring the cardiac rhythm morphology, then immediately activates the pre-trigger memory for temporarily recording diagnostic data. If the predicted arrhythmia occurs, diagnostic data recorded in the pre-trigger memory before and during the arrhythmia is likewise transferred to long-term memory. In either case, once there is no longer an elevated risk of an arrhythmia, the pre-trigger memory is deactivated to save power. In this manner, IEGM data and event record data is advantageously captured during the period of time prior to an arrhythmia and during the arrhythmia itself for subsequent physician review—without requiring that the pre-trigger memory be continuously active throughout the lifetime of the device. Hence, power savings can be achieved as compared to devices that require that the pre-trigger memory be continuously active.

In accordance with a second aspect, techniques are provided for adaptively modifying parameters employed to trigger the recording of diagnostic data, so as to reduce the likelihood of any unnecessary recording of such data. Briefly, diagnostic data is selectively recorded based upon the detection of predetermined recording trigger parameters indicative of the onset of circumstances wherein diagnostic data is to be recorded. Then, the trigger parameters are adaptively modified so as to reduce the likelihood of any unnecessary recording of diagnostic data in the future. In this manner, the parameters employed to activate the recording of diagnostic data—whether predictive or otherwise—are automatically adjusted so as to help ensure that diagnostic data is only recorded in circumstances where it is needed. In other words, the device adaptively learns to record diagnostic data only in circumstances of particular interest, thereby preventing power drain caused by any unnecessary recording of diagnostic data. In one specific example, wherein the recordation of diagnostic data is triggered by some predetermined number of the beats exceeding an upper heart rate threshold (i.e. some number of "fast beats"), the number of fast beats required to trigger diagnostic recording is incrementally adjusted based upon whether the detected fast beats were truly indicative of the onset of arrhythmia.

Preferably, both the risk-based techniques and the adaptive adjustment-based techniques of the invention are implemented so that the implanted device is capable of both (1) controlling the recording of diagnostic data based upon an evaluation of the likelihood that an arrhythmia will occur and (2) automatically adjusting the parameters employed in making the evaluation so as to improve the reliability of such evaluations. For example, the device determines whether a predicted arrhythmia in fact occurred, then adjusts parameters employed to make the prediction to improve further predictions.

In the still other examples, the risk-based techniques are selectively enabled or disabled based upon current patient conditions. In particular, for patients prone to ventricular fibrillation, the detection of any episode of ventricular tachycardia is employed to deactivate the risk-based triggering technique and to instead enable continuous recording of diagnostic data in accordance with otherwise conventional pre-trigger techniques for some extended period of time, such as for nine months. In this manner, if a patient is at risk of a life-threatening arrhythmia, conventional "pre-trigger" diagnostic recording techniques can be employed to ensure that diagnostic data corresponding to all episodes of arrhythmias is recorded in memory—thus eliminating the risk that pre-arrhythmia data for some episodes may be missed due to erroneous predictions. In other words, increased power consumption is tolerated to better ensure that all arrhythmias are properly documented. Then, if no further episodes of ventricular tachycardia are detected during the extended period of time, the risk-based triggering techniques are again enabled to resume power savings.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the system and method. The scope of the invention should be ascertained with reference to the issued claims. In the description that follows, like numerals or reference designators will be used to refer to like parts or elements throughout.

Figure 1:
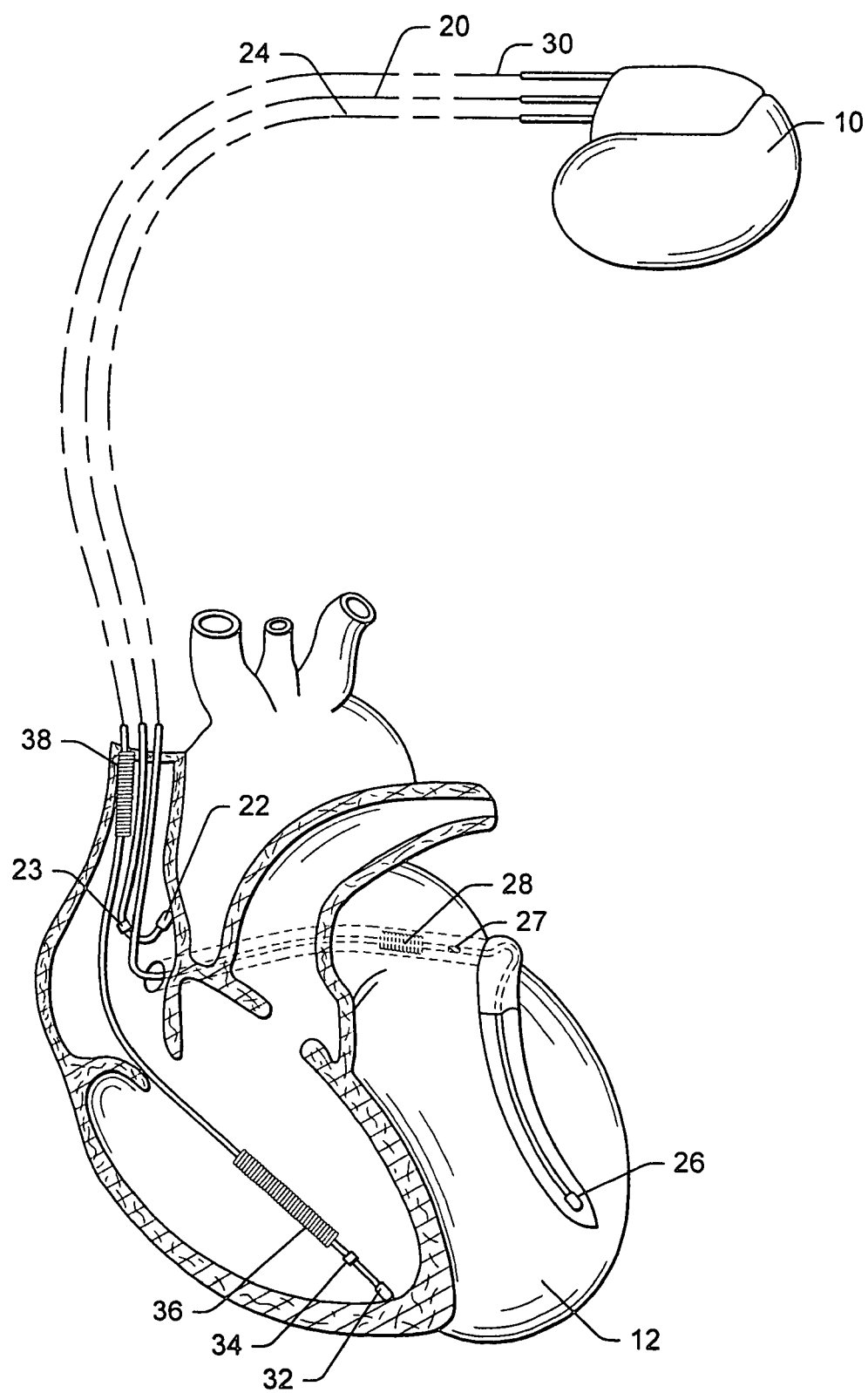
FIG. 1 is a simplified diagram illustrating an implantable stimulation device in electrical communication with at least three leads implanted into the heart of a patient for delivering multi-chamber stimulation and shock therapy.

FIG. 1 illustrates a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "tickle warning" signal, an additional electrode 31 is provided in proximity to the device can.

Figure 2:
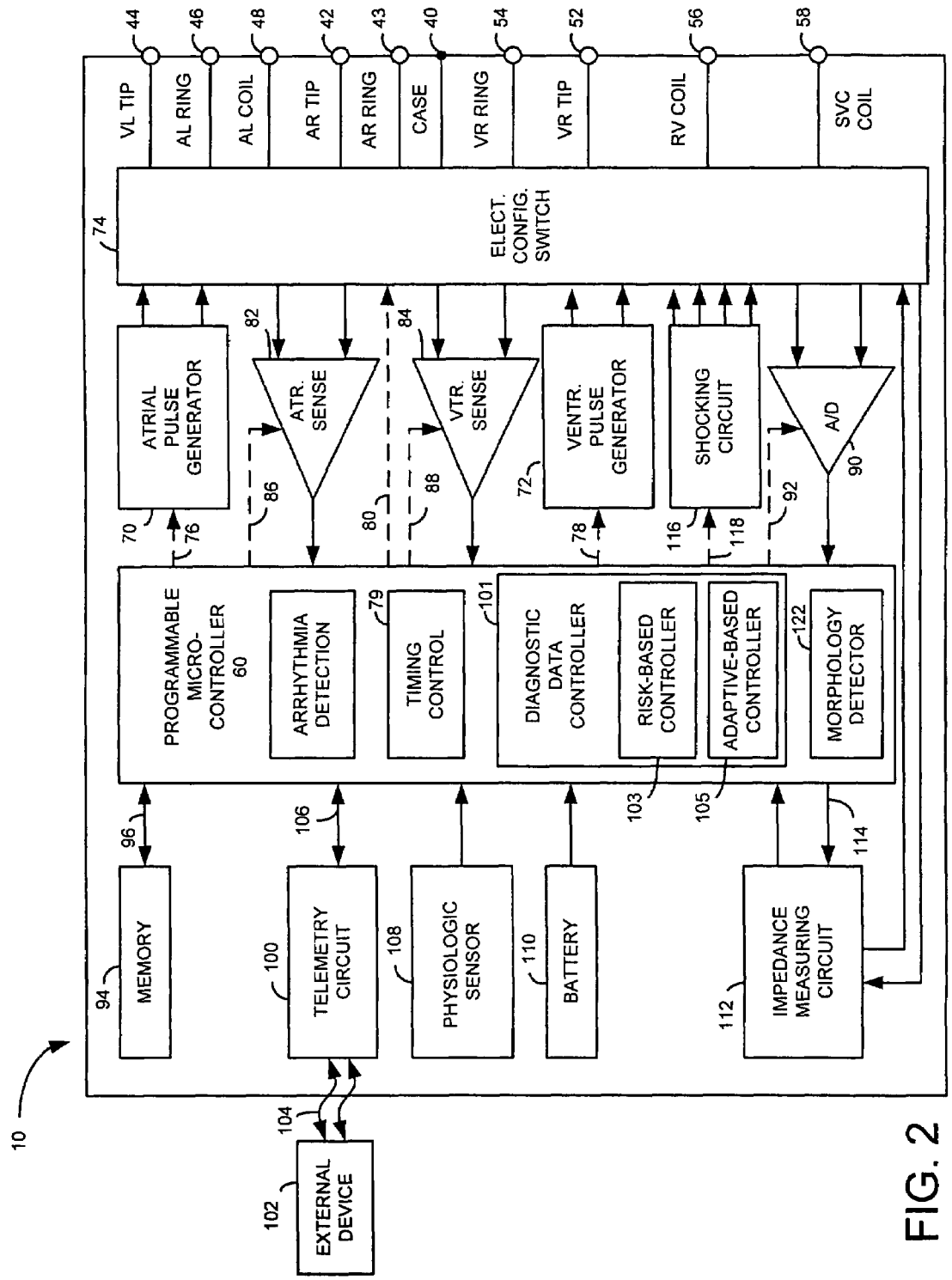
FIG. 2 is a functional block diagram of the stimulation device of FIG. 1, particularly illustrating a diagnostic data controller for controlling the recording of IEGM and other diagnostic data.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to heart 12 within each respective tier of therapy. Other pacing parameters include base rate, rest rate and circadian base rate. A feature according to one illustrative embodiment is the ability to sense and store a relatively large amount of diagnostic data (e.g., from the data acquisition system 90), which data can be subsequently transmitted to an external programming device for review by a physician to help guide in the programming of the device.

With regard to the storage of diagnostic data, microcontroller 60 includes a diagnostic data controller 101 for controlling the recording of IEGM and other diagnostic data in memory 94. Controller 101 includes both a risk-based controller 103 and an adaptive-based controller 105. As will be explained more fully below, controller 101 is capable of exploiting either risk-based techniques or adaptive adjustment-based techniques (or both) in determining when to trigger recording of diagnostic data in memory 94 so as to reduce overall battery drain while still ensuring that data of interest is properly recorded for subsequent review by a physician.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 should have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Referring to the remaining figures, flow charts, graphs and other diagrams illustrate the operation and novel features of stimulation device 10 as configured in accordance with exemplary embodiments. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Overview of the Risk-Based Diagnostic Recording Techniques

Figure 3:
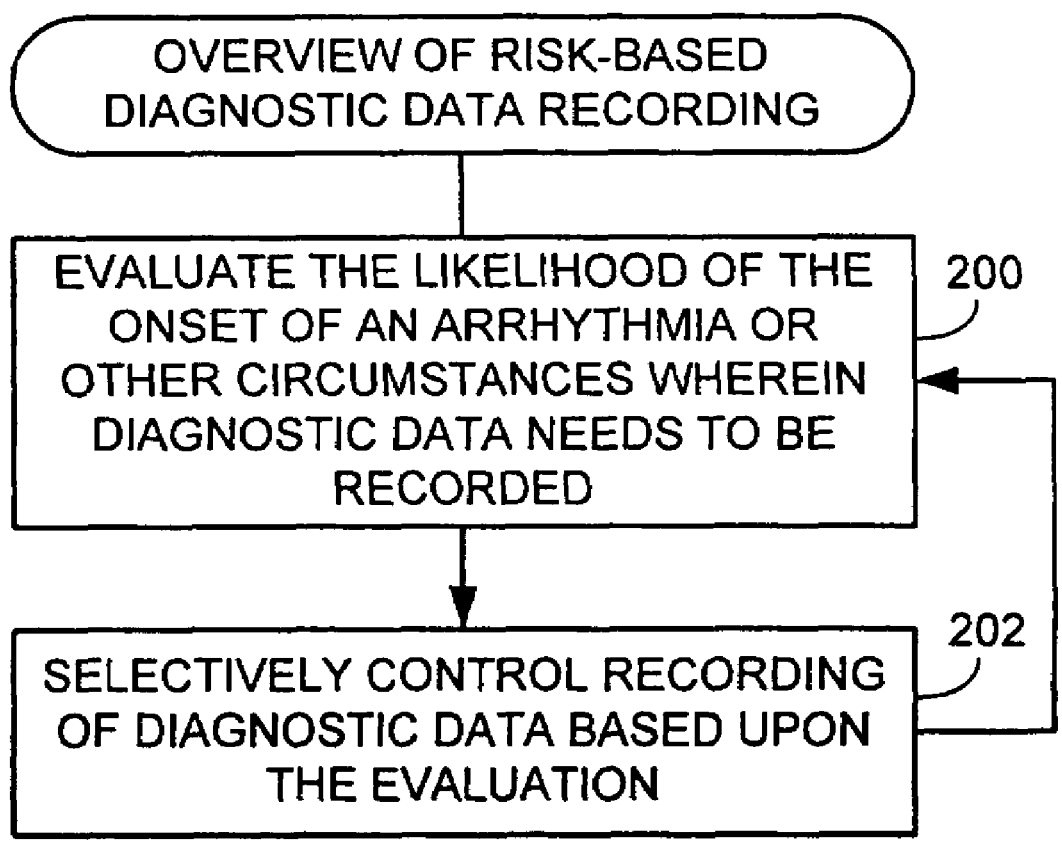
FIG. 3 is a flow chart is providing an overview of risk-based diagnostic data recording techniques performed under the control of the diagnostic controller of FIG. 2.
Figure 4:
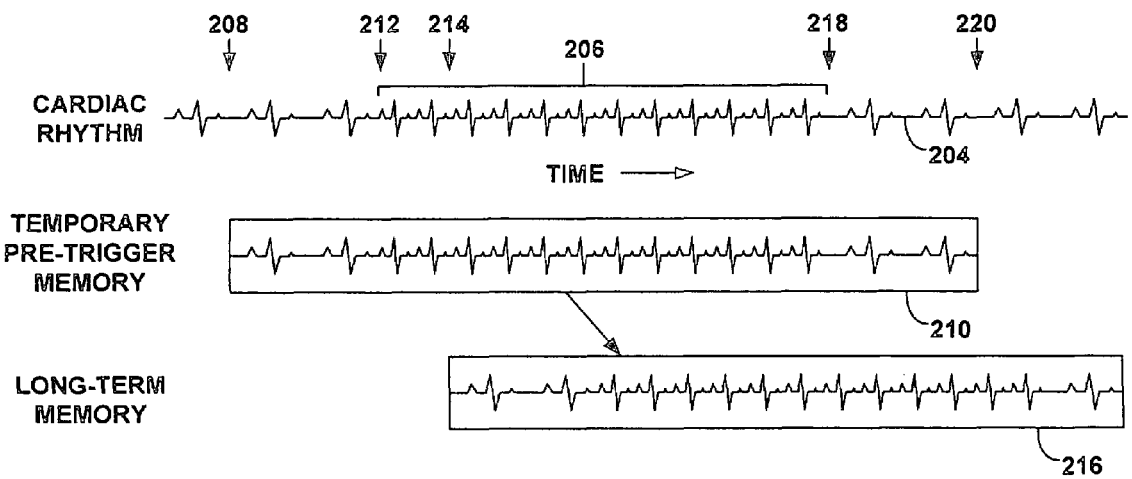
FIG. 4 is a stylized timing diagram illustrating an example of the operation of the risk-based diagnostic data recording technique of FIG. 3.

FIGS. 3-4 provide an overview of the risk-based diagnostic data recording techniques. Briefly, at step 200 of FIG. 3, risk-based controller 103 of the diagnostic controller of the implanted device (FIG. 2) evaluates the likelihood of the onset of circumstances wherein diagnostic data should be recorded, such as by predicting the onset of an arrhythmia based on an analysis of cardiac rhythm morphology. Exemplary risk-based evaluation techniques are discussed below. Then, at step 202, the device selectively controls the recording of diagnostic data based upon the evaluation performed at step 200. Preferably, upon the prediction of an arrhythmia, the device activates the recording of diagnostic data within temporary "pre-trigger" memory so that the diagnostic data detected prior to the arrhythmia (as well as diagnostic data detected during the arrhythmia) are both recorded in temporary memory and can then subsequently be transferred to long-term memory for eventual transmission to an external programmer for review by a physician. Typically, the recording of diagnostic data continues until either the arrhythmia terminates or until a determination is made that no arrhythmia in fact occurred. Techniques for predicting an imminent arrhythmia are set forth in U.S. Pat. Nos. 6,115,627 and 6,516,219, both to Street. Other techniques for predicting arrhythmias are set forth in U.S. Pat. Nos. 6,272,377 and 6,400,982 to Sweeney et al. and U.S. Pat. No. 6,308,094 to Shusterman et al. These patents are incorporated by reference herein.

The risk-based controller may be programmed to predict the onset of an imminent arrhythmia or to instead identify periods of time wherein there is an elevated risk of an arrhythmia, or both. If there is a prediction of an imminent arrhythmia, the diagnostic data is preferably recorded in temporary memory only until the arrhythmia terminates or until a determination is made that no arrhythmia occurred within an expected time frame. If an elevated risk of an arrhythmia is identified, then temporary memory is preferably activated throughout the period of time, at which the patient is at risk, which may be (depending upon the circumstances) hours, days, weeks, or perhaps months. Examples are described below wherein an elevated risk of arrhythmia is identified based upon heart rate variability and wherein an elevated risk of ventricular fibrillation is identified based upon the detection of individual episodes of ventricular tachycardia.

In any case, by recording diagnostic data in temporary memory only in circumstances wherein diagnostic data needs to be recorded, such as during and immediately prior to an imminent arrhythmia or during periods of elevated risk of arrhythmia, considerable power savings are achieved over the devices that continuously recorded diagnostic data in temporary memory at all times throughout the lifetime of the device. Depending upon the particular device and the power source employed savings of six months or more in device longevity can be achieved. By providing for the recording of diagnostic data detected prior to the onset of an arrhythmia, the physician can thereby review the circumstances leading up to the arrhythmia and adjust the programming of the device so as to reduce the likelihood of a similar arrhythmia occurring again. For example, if the device is capable of overdrive pacing, control parameters associated with overdrive pacing may be adjusted by the physician in an effort to prevent the onset of additional arrhythmias. One particularly effective overdrive pacing technique, referred to as dynamic atrial overdrive (DAO) pacing, is described in U.S. Pat. No. 6,519,493 to Florio et al., entitled "Methods And Apparatus For Overdrive Pacing Heart Tissue Using An Implantable Cardiac Stimulation Device".

Although described primarily with reference to the evaluation of the risk of the onset of an arrhythmia, the techniques of FIG. 3 may be exploited to evaluate the likelihood of the onset of any circumstances or event wherein IEGM data or other diagnostic data might preferably be recorded. For example, the device may be configured to predict the onset of vasovagal syncope or cardiac ischemia (such as an acute myocardial infarction (AMI)) or other non-arrhythmic medical events, so that diagnostic data may be recorded prior to and during the event. Techniques for predicting the onset of vasovagal syncope are set forth in U.S. patent application Ser. No. 10/132,044, filed Apr. 24, 2002, which is a CIP of U.S. patent application Ser. No. 09/543,832, of Park et al., entitled "System And Method For Prevention Of Recurrent Vasovagal Syncope Using Cardiac Pacing", filed Apr. 2, 2000, (now abandoned). Techniques for predicting the onset of cardiac ischemia including AMI are set forth in U.S. patent application Ser. No. 10/603,429, of Wang et al., entitled "System And Method For Detecting Cardiac Ischemia Using An Implantable Medical Device", filed Jun. 24, 2003 and in U.S. patent application Ser. No. 10/603,398, of Min et al., entitled "System And Method For Detecting Cardiac Ischemia Based On T-Waves Using An Implantable Medical Device", filed Jun. 24, 2003. These patent applications are incorporated by reference herein.

An example of the risk-based diagnostic data recording technique of FIG. 3 is illustrated with reference to the example of FIG. 4. Briefly, FIG. 4 provides a stylized illustration of a cardiac rhythm 204, including individual heartbeats represented by P-waves, R-waves and T-waves. Within the cardiac rhythm, a brief episode of a tachyarrhythmia 206 is shown. The onset of the arrhythmia is predicted at time 208. So, beginning at time 208, a temporary "pre-trigger" diagnostic data memory 210 (a component of memory 94 of FIG. 2) is activated to begin recording the cardiac rhythm as a digitized IEGM data. The actual arrhythmia commences at time 212 and confirmation of the arrhythmia is made at time 214 based, for example, upon the significantly elevated heart rate. Once the arrhythmia has been confirmed, the data in the temporary memory is transferred to a long-term diagnostic data memory 216 (also a component of memory 94) for subsequent review by a physician following transmission to an external programming device during a follow-up section. The arrhythmia ultimately terminates at time 218 and the device detects the termination of the arrhythmia at time 220, based upon reduction in heart rate. Accordingly, at time 220, the temporary diagnostic data memory 210 is deactivated to save the power. Although only IEGM data is shown in FIG. 4, the diagnostic data recorded in memories 210 and 216 may additionally include event markers, refractory period information, current control parameters of the device (such as current base rates, A/V delay values, etc.) and any other appropriate diagnostic data.

In one specific example, the device is programmed to transfer all of the diagnostic data from the temporary memory into the long-term memory once the arrhythmia is confirmed. The long-term memory then contains all diagnostic data beginning at time 208 and concluding a time 220. In other implementations, only diagnostic data prior to the termination of the arrhythmia (i.e. up to time 218) is a transferred into long-term memory. In the particular example of FIG. 4, the long-term memory additionally records a portion of the diagnostic data subsequent to time 218 so that the physician, during review of the data, can verify that the arrhythmia did indeed terminate.

Overview of the Adaptive-Based Diagnostic Recording Techniques

Figure 6:
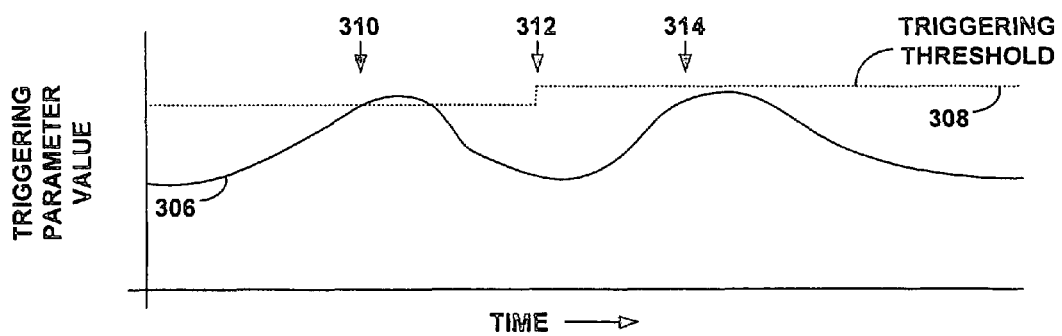
FIG. 6 is a stylized timing diagram illustrating one example of the operation of the adaptively-triggered diagnostic data recording technique of FIG. 5.
Figure 5:
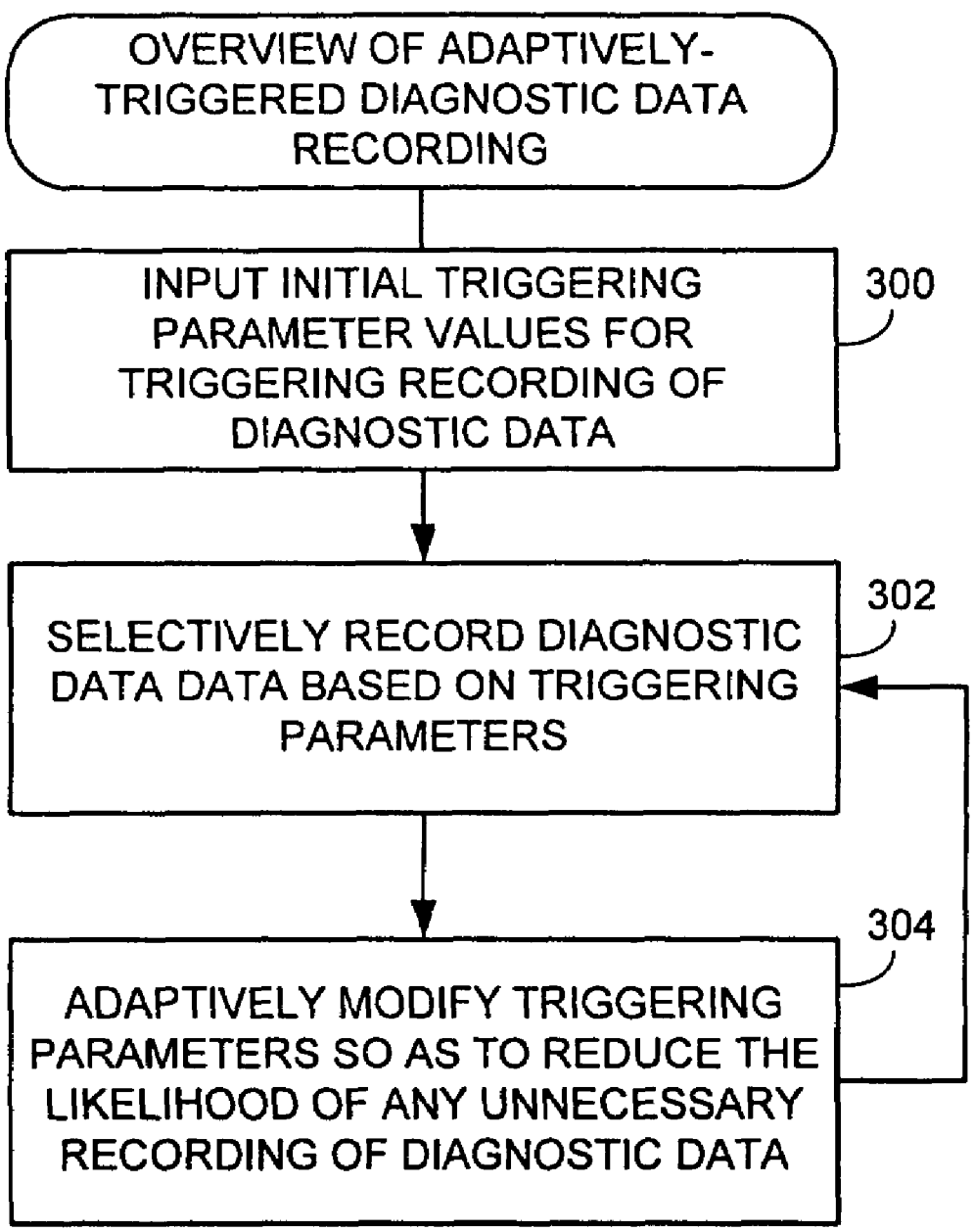
FIG. 5 is a flow chart providing an overview of adaptively-triggered diagnostic data recording techniques performed under the control of the diagnostic data controller of FIG. 2.

FIGS. 5-6 provide an overview of the adaptively-triggered diagnostic data recording techniques. Briefly, at step 300, an initial set of triggering parameters for triggering the recording of diagnostic data are input from memory into diagnostic data controller 101 of the implanted device (FIG. 2). Beginning at step 302, the diagnostic controller selectively records diagnostic data based upon the triggering parameters (such as by comparing numerical values derived from the current cardiac rhythm against the triggering parameters.) In other words, at step 302, if the triggering parameters indicate that diagnostic data should currently be recorded (perhaps because the heart rate exceeds a threshold indicative of an ongoing tachyarrhythmia) then diagnostic data is recorded in memory. As before, preferably, the diagnostic data is first stored in a temporary pre-trigger memory, then transferred to long-term memory only upon subsequent verification that the diagnostic data indeed needed to be recorded (e.g. upon subsequent verification of an on-going arrhythmia). Eventually, during step 302, a determination is made as to when to terminate recording of the diagnostic data (e.g. because the heart rate falls below the tachyarrhythmia threshold). Then, at step 304, after the diagnostic data has been recorded, adaptive-based controller 105 (also FIG. 2) adaptively modifies the triggering parameters input at step 300 so as to reduce the likelihood of any unnecessary recording of diagnostic data.

For example, if triggering parameters are provided to activate the recording of diagnostic data only during an on-going arrhythmia but subsequent examination of the cardiac rhythm indicates that no arrhythmia in fact occurred (i.e. there was a false positive detection of an arrhythmia), then the triggering parameters are adjusted in an effort to improve the reliability of arrhythmia detection. To this end, threshold values used for triggering the recording of diagnostic data may be adjusted upwardly or downwardly as needed. In one specific example, if some threshold number of fast heartbeats are required to trigger the recording of diagnostic data (based on the assumption that the fast beats indicate the onset of a tachyarrhythmia), but no tachyarrhythmia in fact occurred (as evidenced by a quick drop in heart rate), then the threshold number of fast beats is incrementally increased so as to reduce the likelihood of additional false positives. This is described in greater detail below with reference to FIG. 10. In any case, by adaptively modifying the triggering parameter values, the reliability of the triggering values is improved so as to prevent the erroneous recording of diagnostic data in circumstances where the data is not of interest. Hence, power savings are achieved because the memory is not activated in circumstances where it is not actually required and so device longevity is also improved. Moreover, by reducing the likelihood that diagnostic data is recorded in circumstances where it is not of interest, the physician need not spend time reviewing diagnostic data that had been erroneously recorded.

Techniques for adaptively modifying thresholds or other parameters within implantable medicals devices are set forth in U.S. Pat. No. 6,445,949 to Kroll entitled "Implantable Cardioversion Device With A Self-Adjusting Threshold For Therapy Selection", which is incorporated by reference herein. Note that the triggering parameters need not necessarily be predictive parameters or risk-based parameters. Hence, the technique of FIG. 5 is not limited to situations wherein the implanted device predicts the onset of an arrhythmia or makes any evaluation of the likelihood of the onset of prospective events. Rather the technique of FIG. 5 is broadly applicable to situations wherein the implanted device triggers the recording of diagnostic medical data based upon any circumstance of interest.

FIG. 6 provides an example of the adaptive adjustment of a triggering threshold performed in accordance with techniques of FIG. 5. Briefly, an exemplary triggering parameter value 306 is shown, which varies with time. The triggering parameter may be, for example, a numerical value representative of heart rate or heart rate variability, or a numerical parameterization of the morphology of the cardiac rhythm, or some combination thereof. (The corresponding cardiac rhythm is not shown.) In any case, the triggering parameter is compared against a triggering threshold 308 and, if it exceeds the threshold, the pre-trigger memory is activated to store diagnostic data. In the example of FIG. 6, the triggering threshold is intended to be indicative of the onset of a tachyarrhythmia. The triggering parameter exceeds the threshold at 310, thus activating storage of diagnostic data in a temporary memory (such as the pre-trigger memory shown in FIG. 4). In the example of FIG. 6, the detection of the onset of a tachyarrhythmia based on the triggering parameters is erroneous and no sustained tachyarrhythmia occurs. The adaptive-based controller ultimately determines that the prediction was erroneous at time 312. Accordingly, at that point in time, the triggering threshold is incrementally increased to reduce the likelihood of additional erroneous tachyarrhythmia detections. As can be seen, the triggering parameter value again peaks at time 314. However, because the triggering threshold has been increased, the pre-trigger memory is not activated, thereby saving power.

Ultimately, depending upon changes in the triggering parameter and upon the accuracy of subsequent predictions, the triggering threshold may be increased again in response to additional false positive arrhythmia detections or may be decreased in response to the subsequent detection of an arrhythmia that was not properly predicted. Although the example FIG. 6 illustrates a single upper threshold against which the triggering parameter value is compared, in other examples, both upper and lower thresholds are used. In addition, several different triggering parameter values may be compared against respective thresholds with the diagnostic data recording being triggered if at least one of the individual parameters exceeds its corresponding threshold or, in other implementations, only if all of the parameters exceed their respective thresholds. As can be appreciated, a wide range of options are available consistent with the general principles of the embodiments described herein.

Figure 7:
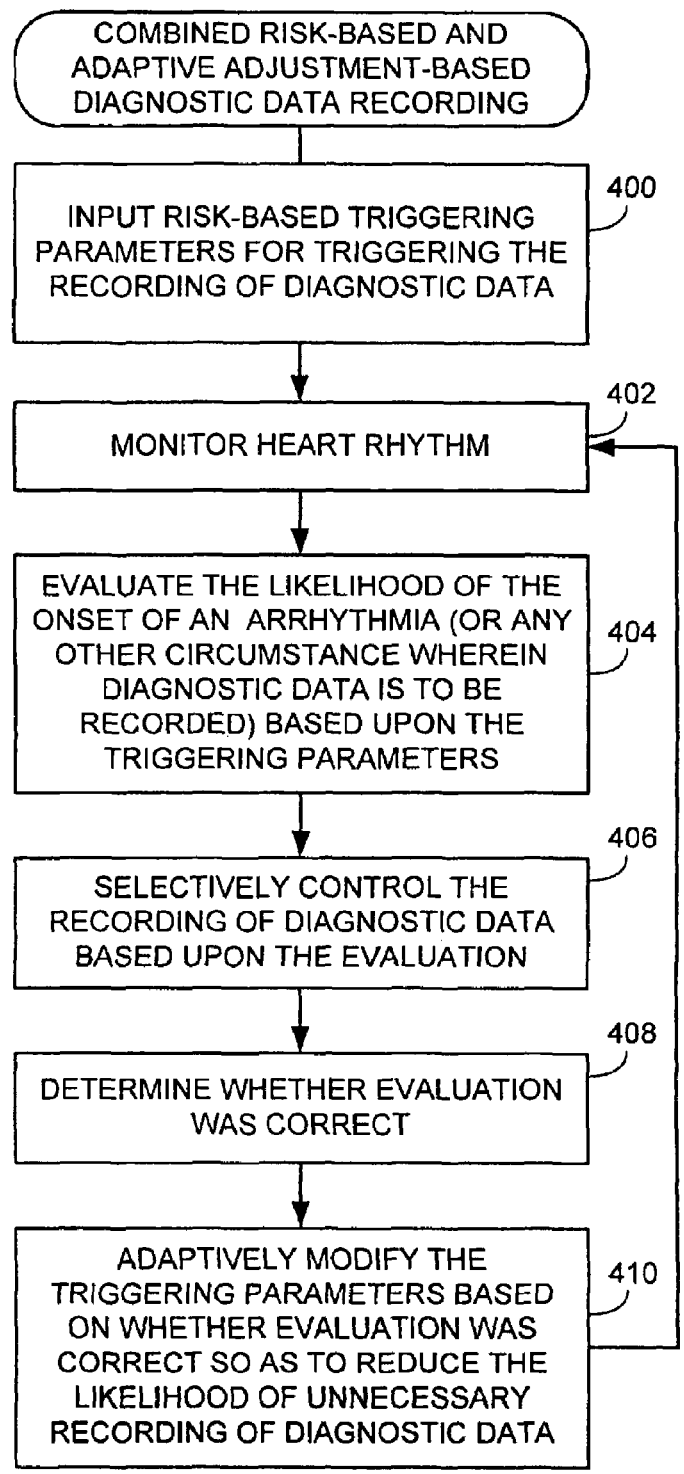
FIG. 7 is a flow chart providing an overview of combined risk-based and adaptive adjustment-based diagnostic data recording techniques performed under the control of the diagnostic data controller of FIG. 2.

Overview of Combined Risk-Based/Adaptive-Adjustment Based Diagnostic Recording Techniques The risk-based and adaptive adjacent-based techniques of FIGS. 3-6 may be combined so as to (1) evaluate the likelihood of the onset of an arrhythmia (or other circumstances requiring the record of diagnostic data) and then (2) adaptively modify risk-based triggering parameters to improve the reliability of additional evaluations. This is summarized by the flowchart of FIG. 7. Initially, at step 400, the diagnostic data controller (system 101 of FIG. 2) inputs risk-based triggering parameters for use in triggering the recording of diagnostic data. Beginning at step 402, the controller monitors heart rhythm and, at step 404, evaluates the likelihood of the onset of circumstances wherein diagnostic data needs to be recorded (such as by predicting the onset of an arrhythmia.) The evaluation is based upon the initial triggering parameters input at step 400. Then, at step 406, the controller selectively activates and deactivates the recording of diagnostic data based upon the evaluation. Preferably, the diagnostic data is first stored in a temporary pre-trigger memory for subsequent transfer to long-term memory upon subsequent verification of the arrhythmia or other circumstance necessitating diagnostic data recordation. As explained above, diagnostic data is preferably recorded prior to the onset of an arrhythmia so that the physician may subsequently review of the circumstances leading up the arrhythmia. In any case, at step 408, the controller determines whether the evaluation performed at step 404 was correct. In the case of an arrhythmia prediction, the adaptive-based controller merely determines whether the predicted arrhythmia actually occurred within an expected time frame. In the case where the risk-based controller instead merely identifies the increased likelihood of an arrhythmia, the adaptive-based controller determines whether an arrhythmia occurred at any point during the period of time of increased likelihood. Then, at step 410, the controller adaptively modifies the triggering parameters based upon whether the evaluation was correct, in an effort to reduce the likelihood of any unnecessary activation of the pre-trigger memory in the future.

For example, at step 410, if a prediction was made that was incorrect; the parameters are adjusted so as to prevent similar erroneous predictions from occurring again. If the prediction was correct, then either the triggering parameters are not adjusted or the parameters are slightly adjusted so as to narrow the range of circumstances in which an arrhythmia prediction is made so as to refine the evaluation capabilities. The extent to which parameters are adjusted depends up on the particular parameters and upon the "certainty" of the prior prediction. If an erroneous prediction had merely indicated a 10% risk of the onset of an arrhythmia, the triggering parameters are not adjusted as much as if the erroneous predication had indicated a 90% risk. Also, circumstances may arise wherein an arrhythmia occurs which was not predicted, in which case the triggering parameters are adjusted at step 410 to broaden the range in which such predictions occur. Hence, with this technique, the triggering parameters may be adjusted either up or down to fine-tune the parameters to maximize the reliability of predictions or any other evaluations made based on the parameters. Frequent adjustment of triggering parameters helps compensate for any changes in the patient (such as may arise as a result of medication or the progression or regression of heart disease), which may affect the accuracy of predictions and other evaluations.

With reference to the remaining figures, various exemplary techniques that exploit the adaptive and risk-based features will now be described.

Heart Rate Variability-Based Triggering Techniques

Figure 8:
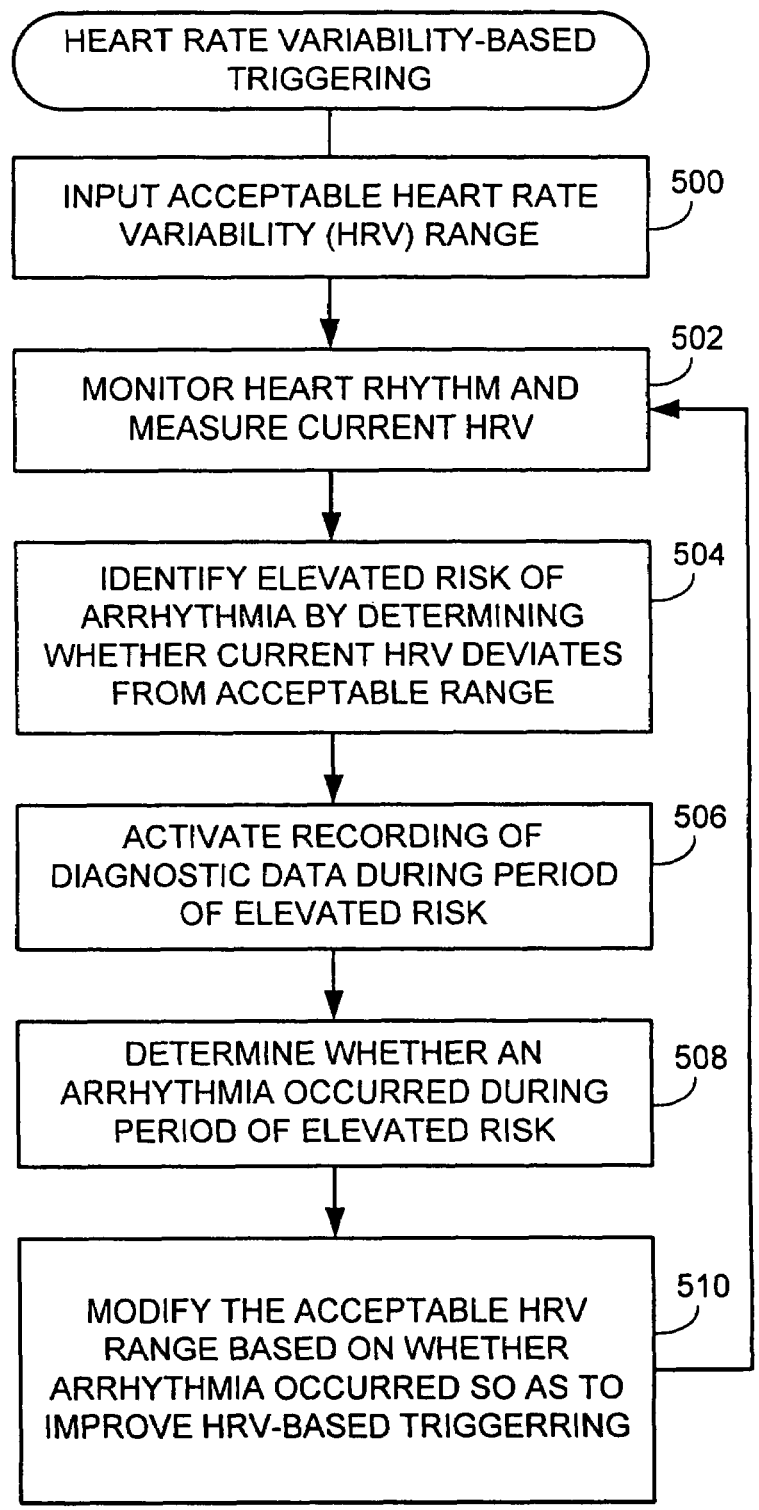
FIG. 8 is a flow chart providing an example of the combined technique of FIG. 7 wherein heart-rate variability is exploited.

Referring next to FIG. 8, a heart rate variability-based triggering technique is illustrated. Initially, at step 500, the controller inputs an acceptable heart rate variability range, which may be defined in terms of both an upper and lower limits on acceptable variability. This is because both excessively high and excessively low heart rate variability are indicative of possible onset of arrhythmia. Excessively low heart rate variability is often a precursor of ventricular tachyarrhythmias. Excessively high heart rate variability may be a precursor to other arrhythmias, particularly atrial arrhythmias triggered by frequent ectopic beats. It should be noted that this technique employs a definition of heart rate variability that is slightly different from the conventional definition. The conventional heart rate variability calculations attempt to remove ectopic beats before performing any statistics. As an alternative embodiment, not shown, the method will perform classical heart rate variability analysis but only watch for variation on the low side.

In any case, beginning at step 502, the diagnostic data controller (system 101 of FIG. 2) monitors heart rhythm and measures the current degree of heart rate variability using any appropriate technique. An example of one technique for measuring heart rate variability is set forth in U.S. Pat. No. 5,941,831 to Turcott, entitled "Method For Diagnosing Cardiac Arrhythmias Using Interval Irregularity", which is incorporated by reference herein. Other techniques for accessing a degree of randomness in the heart rate are set forth in U.S. patent application Ser. No. 10/017,836, of Kroll et al., entitled "Dynamic Control Of Overdrive Pacing Based On Degree Of Randomness Within Heart Rate", filed Dec. 12, 2001, which is also incorporated by reference herein.

At step 504, the diagnostic controller determines whether there is an elevated risk of an arrhythmia based upon the current degree of heart rate variability by determining whether its deviates from the acceptable range input at step 500. Techniques for identifying an elevated risk of arrhythmia based upon heart rate variability are set forth in U.S. Pat. No. 6,035,233 to Schroeppel et al., entitled "Implantable Medical Device Responsive To Heart Rate Variability Analysis", which is incorporated by reference herein. If an elevated risk of arrhythmia is identified then, at step 506, the controller records IEGM data and other diagnostic data in accordance with techniques are already summarized, i.e. the temporary "pre-trigger" memory is activated so that data leading up to an arrhythmia as well as data recorded during an arrhythmia can be saved for subsequent review. Diagnostic data is recorded in the pre-trigger memory throughout the period of time during which there is an elevated risk, which, depending upon the circumstances, may last for hours, days, weeks or months. Typically, the elevated risk is deemed to last so long as the HRV remains outside the acceptable range. (Note that, with pre-triggered memory implemented as a FIFO queue, diagnostic data stored therein may be overwritten with new diagnostic data during the period of elevated risk. However, if an arrhythmia occurs, the data recorded during and immediately prior to the arrhythmia are transferred to long-term memory before the data is overwritten by new data.)

Eventually, at step 508, a determination is made as to whether any arrhythmias occurred during the period of elevated risk and, at step 510; the controller modifies the acceptable heart rate variability threshold values accordingly. To this end, the upper and lower threshold values are incrementally increased or decreased, as needed, based upon whether an arrhythmia occurred. Typically, if no arrhythmia occurred, the HRV thresholds are narrowed to reduce the likelihood that the pre-trigger memory will again be activated in circumstances where no arrhythmias subsequently occur. If an arrhythmia occurs even though the current HRV was within acceptable bounds, the HRV thresholds are expanded to better ensure that the pre-trigger memory will be active the next time an arrhythmia does occur. Also, note that, depending-upon how quickly heart rate variability changes, a prediction of an imminent arrhythmia may also be made base on heart rate variability. Thus, heart rate variability is not necessarily limited to merely identifying an increased likelihood of an arrhythmia over an extended period of time.

Morphology-Based Triggering Techniques

Figure 9:
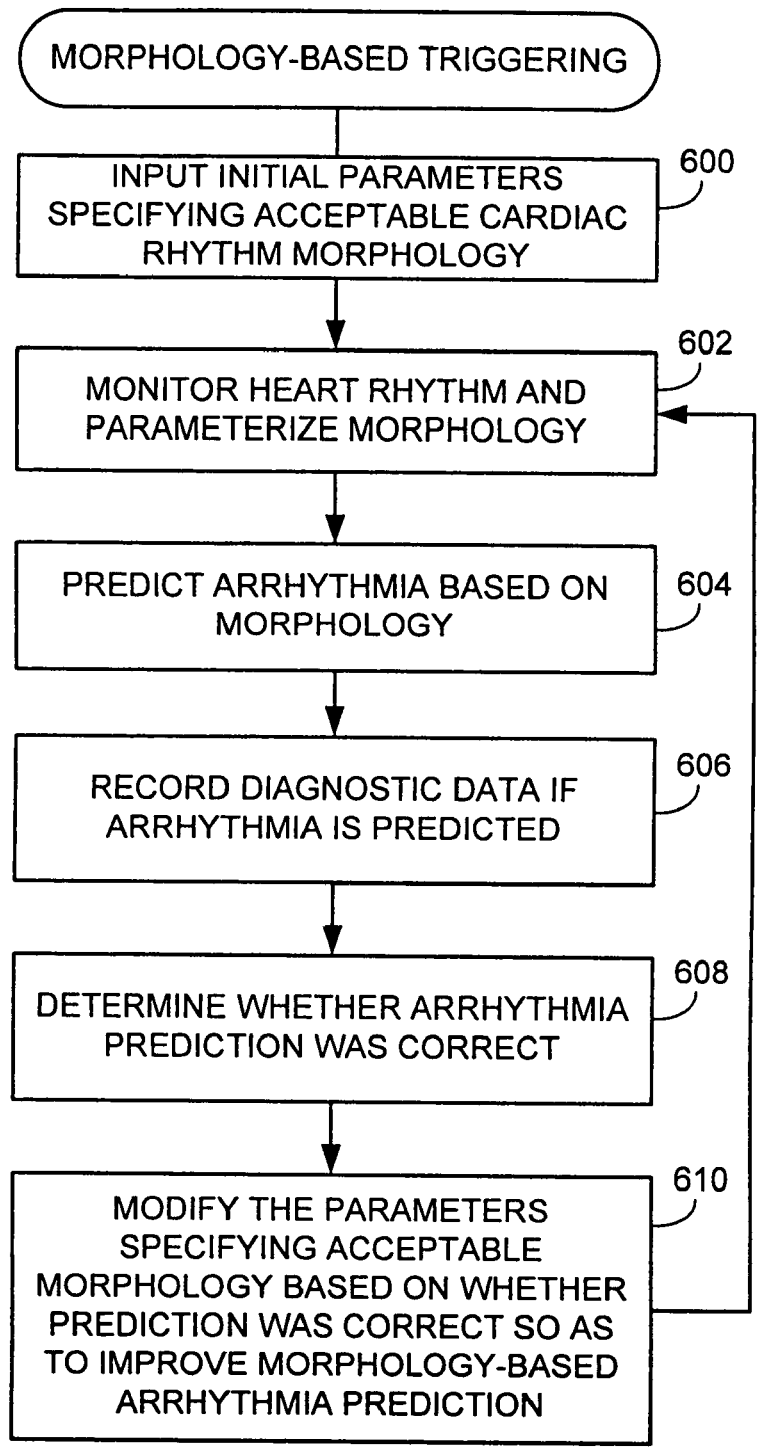
FIG. 9 is a flow chart providing an example of the combined technique of FIG. 7 wherein cardiac rhythm morphology is exploited.

FIG. 9 summarizes a morphology-based prediction technique. Here, rather than comparing a numerical heart rate variability value against predetermined upper and lower thresholds, the device evaluates the morphology of the cardiac rhythm and compares the morphology against a range of acceptable values representative of acceptable morphology. Briefly, at step 600, the diagnostic data controller (system 101 of FIG. 2) inputs parameters specifying acceptable cardiac rhythm morphology. Morphology can be numerically parameterized using techniques set forth in U.S. Pat. No. 6,304,773, which incorporated by reference herein. Techniques for predicting arrhythmias based on morphology are set forth in the aforementioned patents to Sweeney et al. (U.S. Pat. Nos. 6,272,377 and 6,400,982.) Alternatively, acceptable shapes for particular cardiac events, such as QRS-complexes, are stored as templates so that digitized versions of the newly detected cardiac events can be compared with the templates to determine whether they are within a suitable range. In any case, beginning at step 602, the controller monitors heart rhythm and parameterizes the morphology, either numerically or via the template-based approach, or any other suitable approach. At step 604, an arrhythmia prediction is made based upon changes in morphology and, at step 606, IEGM data and other diagnostic data are recorded, preferably first using a pre-trigger memory. At step 608, the diagnostic controller determines whether the predicted arrhythmia actually occurred and also identifies circumstances wherein arrhythmias occurred that had not been predicted. At step 610, the diagnostic controller then modifies the parameters used for specifying acceptable morphology, based upon whether the prediction was correct so as to improve further morphology-based arrhythmia predictions.

In implementations wherein morphology is parameterized by a numerical value, thresholds based upon the numerical values are incrementally increased or decreased as needed. In implementations wherein acceptable morphology is represented by templates of QRS-complexes and the like, pre-stored templates are adjusted to represent a broader or narrower range of acceptable shapes. As can be appreciated, a wide range a specific techniques for making morphology-based predictions and for adaptively adjusting morphology-based triggering parameters can be employed and no attempt is made herein to describe all such techniques.

Fast Beat-Based Triggering Techniques

Figure 10:
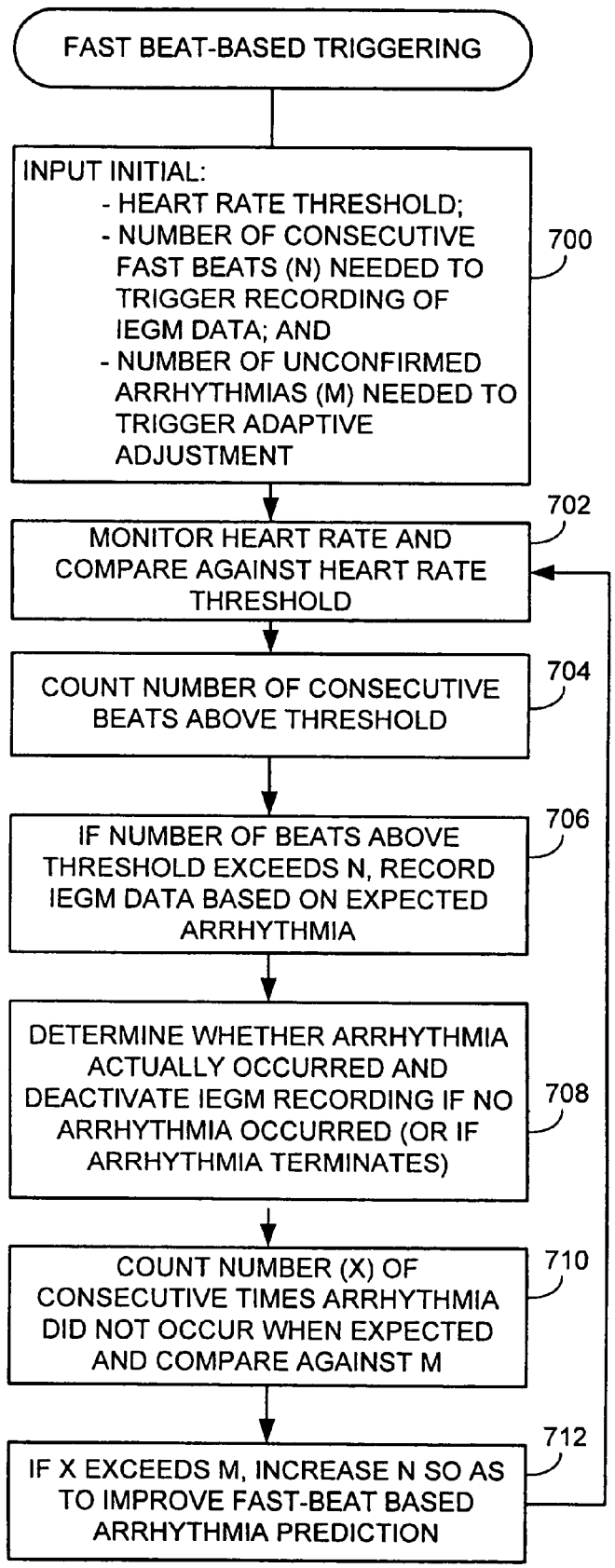
FIG. 10 is a flow chart providing an example of the combined technique of FIG. 7 wherein fast-beats are counted.

FIG. 10 illustrates a fast beat-based triggering technique, which identifies the onset of an arrhythmia based upon some predetermined number of consecutive fast-beats, i.e. beats which exceeded an upper rate threshold, such as 150 beats per minute. At step 700, the diagnostic data controller (system 101 of FIG. 2) inputs: (1) an upper heart rate threshold; (2) the pre-determined number of consecutive fast beats (N) needed to trigger recording of diagnostic data; and (3) an adaptive adjustment threshold (M) representing the number of unconfirmed arrhythmia episodes needed to trigger an adaptive adjustment of the number of fast beats (N). Essentially, the heart rate threshold defines what is meant by a "fast beat". Any beat exceeding that threshold is a fast beat. If N consecutive beats exceed the threshold, an arrhythmia is deemed to have commenced. As will be explained below, the adaptive adjustment threshold (M) is a separate threshold value used to determine whether an adaptive adjustment to the triggering value should be made.

Beginning at step 702, the controller monitors heart rate and compares it against the heart rate threshold. At step 704, the controller counts the number of consecutive beats above the threshold and, at step 706, if the number of beats exceeds the threshold, then diagnostic data is recorded. At step 708, the controller then determines whether an arrhythmia in fact occurred by continuing to monitor the intrinsic heart rate of the patient. If the rate remains above the pre-determined upper rate threshold for an extended period of time, then an arrhythmia is deemed to have occurred. If the heart rate instead drops below the upper rate threshold, indicating that the few consecutive beats above that threshold were probably anomalous, then a conclusion is drawn that no arrhythmia in fact occurred. In other words, at step 708, the controller determines whether the fast beats initially detected were indeed indicative of an actual arrhythmia and, if not, diagnostic data recording is deactivated. Diagnostic data recording is also deactivated after an actual arrhythmia eventually terminates.

At step 710, the controller counts the number of consecutive times (X) that an arrhythmia did not actually occur in circumstances where one was deemed to have commenced. In other words, X is a count of consecutive "false positives". The count (X) is then compared against the aforementioned adaptive adjustment threshold (M) at step 712 and, if X exceeds M, then the value of N is automatically increased so as to improve fast-beat-based arrhythmia prediction. In one example, the adaptive adjustment threshold value is set to 2 and the number of consecutive beats needed to trigger the recording of diagnostic data (N) is initially set in the range of 1 to 3. Taking an example wherein N is initially set to 3, whenever three consecutive fast-beats occur, the controller immediately begins recording diagnostic data based on the assumption that an arrhythmia has commenced (i.e. the pre-trigger memory is activated at that time.) If diagnostic data recording is triggered on two consecutive occasions wherein no arrhythmia was subsequently confirmed, then the value N is increased to 4 so that it will then require four consecutive fast beats to trigger diagnostic data recording. These are merely exemplary values, which can be programmed by the physician using an external programmer based upon the particular needs the patient. In addition, at step 712, the value N is periodically decreased to ensure that it does not remain unnecessarily high. In other implementations, the heart rate threshold itself is adaptively adjusted.

Ventricular Tachycardia-Based Control Techniques

In the foregoing, embodiments are illustrated wherein the recording of diagnostic data is activated or deactivated based upon various triggering conditions. Additionally, however, otherwise conventional pre-trigger diagnostic data recording can be employed, but with the pre-trigger techniques selectively enabled or disabled based on patient conditions. This is illustrated FIG. 11 wherein the detection of at least one episode of ventricular tachycardia is employed to enable otherwise conventional pre-trigger diagnostic data recording for extended periods of time, such as for nine months, to ensure that all possible episodes of arrhythmia are captured (along with the IEGM leading up to the arrhythmia). This is provided because ventricular tachycardia is often a precursor to ventricular fibrillation or other life-threatening arrhythmias. Accordingly, within patients prone to ventricular fibrillation, diagnostic data is recorded continuously in temporary pre-trigger memory to ensure that it can be saved in the event an arrhythmia occurs. This ensures that no arrhythmias are missed as result of faulty predictions. In the patients for whom no ventricular tachycardia occurs, then the power-saving techniques described above are exploited to increase device longevity (at the risk of occasionally failing to record precursor data to an arrhythmia which does in fact occur.)

Briefly, at step 800, the diagnostic data controller (system 101 of FIG. 2) monitors cardiac rhythm and selectively records diagnostic data based on the risk-based/adaptive adjustment techniques discussed above. At step 802, the controller monitors for ventricular tachycardia and, if detected, the controller deactivates the risk-based/adaptive adjustment techniques and instead continuously records diagnostic data using FIFO pre-trigger memory for a predetermined, extended period of time (such as nine months). If no additional episodes of the ventricular tachycardia occur during that period of time, then the device reverts to step 800 where the controller again activates risk-based and adaptive adjustment techniques to reduce overall power consumption. In other words, with the technique of FIG. 11, once a single episode of ventricular tachycardia is detected, the pre-trigger memory is switched on and the risk-based controller and the adaptive-adjustment controller of FIG. 2 are deactivated until the nine month period has elapsed. By deactivating the risk-based controller and the adaptive-adjustment controller, processing demands on the microprocessor are reduced. Alternatively, these components may be programmed to remain activate during the nine month period. In that case, the components would not operate to activate or deactivate the pre-trigger memory during that time. However, the components would nevertheless continue to operate to predict the onset of specific arrhythmias or other medical events and to continue to adaptively adjust triggering parameters so that, once the nine month period has elapsed, improved arrhythmia predictions may be achieved.

Figure 11:
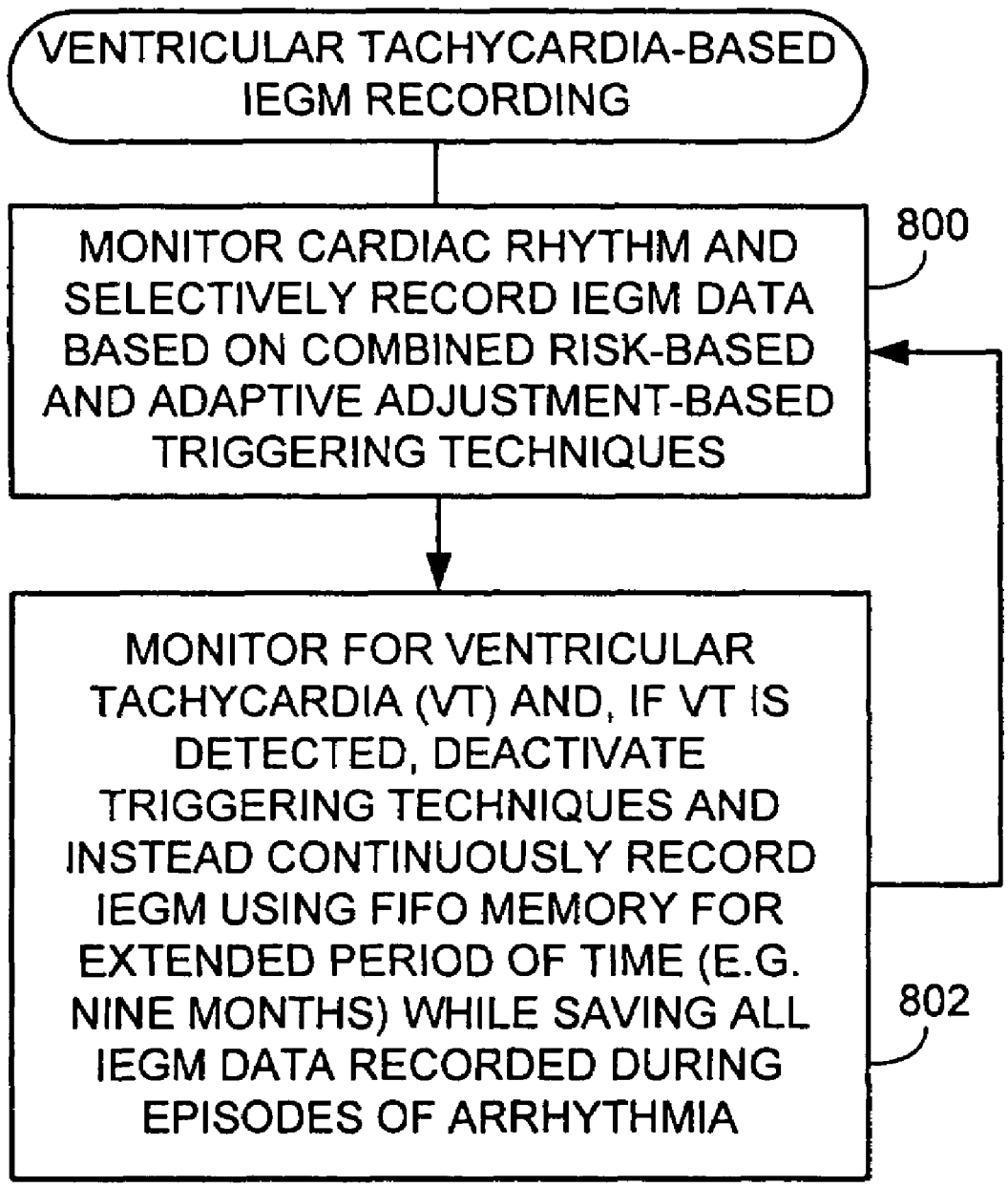
FIG. 11 is a flow chart providing an overview of ventricular tachycardia-based diagnostic data control techniques performed under the control of the diagnostic controller of FIG. 2.

Although FIG. 11 is described with respect to the ventricular tachycardia, other circumstances can be employed for selectively enabling or disabling the risk-based triggering and the adaptive adjustment techniques. In addition, depending upon the implementation, either only the risk-based but not the adaptive techniques may be enabled or only the adaptive but not the risk-based techniques are enabled. As can be appreciated, a wide range of implementation options are available consistent with the principles of the embodiments described herein.

In general, various different risk-based techniques can be combined to improve the reliability of predictions. For example, the device can be configured to perform heart rate variability-based, morphology-based, and fast beat-based arrhythmia prediction, rather than exploiting just one risk-based technique. In this regard, values representative of heart rate variability, morphology, and fast beats may be numerically combined to provide a single "metric" value for comparison against a combined threshold for determining whether an arrhythmia is imminent or has commenced. Techniques for combining different parameters into a single metric value for evaluation are set forth in U.S. patent application Ser. No. 10/339,989, to Koh et al., entitled "System And Method For Detecting Circadian States Using An Implantable Medical Device", filed Jan. 10, 2003, which is incorporated by reference herein.

While particular embodiments have been described herein, modifications can be made thereto without departing from the spirit and scope of the invention. In particular, although described primarily with reference to an example wherein the implanted device is a defibrillation/pacer, the embodiments described herein are equally applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments described herein are merely illustrative and should not be construed as limiting the scope of the invention.

What is claimed is:

1. An implantable medical device comprising:
a device operative to monitor cardiac rhythm;
an implantable housing having therein a temporary memory operative to record diagnostic data corresponding to the cardiac rhythm; and a long-term memory interfacing with the temporary memory and operative to record diagnostic data stored in the temporary memory; and
a processor operative to:
evaluate the cardiac rhythm for the detection of predetermined recording triggers indicative of an impending cardiac arrhythmia, wherein the cardiac arrhythmia indicated as impending, is not currently present;
control the recording of diagnostic data such that no data is recorded in the temporary memory until the detection of an impending cardiac arrhythmia, wherein the cardiac arrhythmia indicated as impending, is not currently present and no data is transferred from the temporary memory and recorded in the long-term memory until it has been determined that a cardiac arrhythmia did actually occur; and
adaptively modify the recording triggers so as to reduce the likelihood of any unnecessary recording of diagnostic data in the temporary memory.

2. The device of claim 1 wherein the diagnostic data to be recorded includes one or more of: intracardiac electrograms (IEGMs) and event records.

3. The device of claim 1 wherein to control the recording of diagnostic data such that no data is recorded in the temporary memory until the detection of predetermined recording triggers, the processor is further operative to:
receive initial trigger parameters for triggering the recording of diagnostic data in the temporary memory;
monitor cardiac rhythm; and
selectively control the recording of diagnostic data in the temporary memory based on the cardiac rhythm and the trigger parameters.

4. The device of claim 3 wherein the trigger parameters include threshold values against which features of the cardiac rhythm are compared.

5. The device of claim 4 wherein the threshold values include one or more of: heart rate variability threshold values, morphology threshold values, and fast beat threshold values.

6. The device of claim 4 wherein to adaptively modify the recording triggers the processor is further operative to selectively adjust the threshold values so as to reduce the likelihood of any unnecessary recording of diagnostic data in the temporary memory.

7. The device of claim 1 wherein to adaptively modify the recording triggers the processor is further operative to:
    determine whether the recording triggers were properly indicative of an impending cardiac arrhythmia; and
    if not, adjust the recording triggers to more effectively an impending cardiac arrhythmia.

8. The device of claim 7 wherein the recording triggers are indicative of the onset of an arrhythmia and wherein the recording triggers are adjusted based upon whether an arrhythmia in fact occurred.

9. The device of claim 8 wherein to evaluate the likelihood of an impending cardiac arrhythmia, the processor is further operative to detect the onset of an arrhythmia and wherein to control the recording of diagnostic data such that no data is recorded in the temporary memory until the detection of predetermined recording triggers, the processor is further operative to activate recording in the temporary memory upon detection of the onset of the arrhythmia.

10. The device of claim 9 wherein to monitor cardiac rhythm to detect the onset of an arrhythmia the processor is further operative to:
    count a number of beats occurring at a rate above a predetermined rate threshold and detect the onset of an arrhythmia based on detection of a predetermined number of beats having a rate above the rate threshold.

11. The device of claim 10 wherein the predetermined number of beats having a rate above the rate threshold is in the range of one to three beats.

12. The device of claim 10 wherein the processor is further operative to confirm that an arrhythmia actually occurred and, if the arrhythmia is not confirmed, deactivate the recording of diagnostic data in the temporary memory.

13. The device of claim 9 wherein to adaptively modify the recording triggers so as to reduce the likelihood of any unnecessary recording of diagnostic data in the temporary memory the processor is further operative to selectively increment the number of beats required to trigger activation of the recording of diagnostic data in the temporary memory, if the arrhythmia is not confirmed.

14. The device of claim 13 wherein the processor is further operative to selectively increment the number of beats required to trigger activation of the recording of diagnostic data in the temporary memory upon detection of two consecutive episodes wherein the recording of diagnostic data was activated but the arrhythmia was not subsequently confirmed.

15. The device of claim 1 wherein to control the recording of diagnostic data such that no data is recorded in the temporary memory until the detection of predetermined recording triggers indicative of an impending cardiac arrhythmia, the processor is further operative to:
    evaluate the likelihood of an impending cardiac arrhythmia; and
    control the recording of diagnostic data based upon such an evaluation.

16. The device of claim 15 wherein to evaluate the likelihood of an impending cardiac arrhythmia, the processor is further operative to identify periods of time wherein there is an elevated risk of an arrhythmia and wherein to control the recording of diagnostic data such that no data is recorded in the temporary memory until the detection of predetermined recording triggers indicative of an impending cardiac arrhythmia, the processor is further operative to record the data in the temporary memory during the period of time wherein there is an elevated risk of an arrhythmia.

17. The device of claim 16 wherein to identify periods of time wherein there is an elevated risk of an arrhythmia the processor is further operative to monitor heart rate variability and to identify periods of time with reduced heart rate variability.

18. The device of claim 15 wherein to evaluate the likelihood of an impending cardiac arrhythmia, the processor is further operative to predict the onset of an arrhythmia and wherein to control the recording of diagnostic data such that no data is recorded in the temporary memory until the detection of predetermined recording triggers, the processor is further operative to activate recording in the temporary memory prior to the predicted onset of the arrhythmia.

19. The device of claim 18 wherein to predict the onset of an arrhythmia the processor is further operative to monitor cardiac rhythm.

20. The device of claim 19 wherein to monitor cardiac rhythm to predict the onset of an arrhythmia the processor is further operative to:
    examine the morphology of heart beats and predict the onset of an arrhythmia based on detection of a significant change in morphology.

21. A method performed by an implantable medical device, the method comprising:
    evaluating the likelihood of an impending cardiac arrhythmia, wherein an impending cardiac arrhythmia is an arrhythmia that is not currently present and wherein diagnostic medical data is to be recorded in an implanted long-term memory;
    controlling the recording of diagnostic data based upon such an evaluation such that diagnostic medical data is first recorded in an implanted temporary memory only after it is determined that a cardiac arrhythmia that is not currently present is likely to arise, wherein the implanted temporary memory interfaces with the implanted long-term memory;
    determining whether the impending cardiac arrhythmia actually occurred;
    if such cardiac arrhythmia did actually occur, transferring the diagnostic data recorded in the implanted temporary memory to the implanted long-term memory; and
    if such cardiac arrhythmia did not occur, adaptively modifying parameters employed to evaluate the likelihood of such cardiac arrhythmia so as to reduce the risk of unnecessarily recording of diagnostic data in the implanted temporary memory.

22. An implantable medical device comprising:
    an implantable housing having therein a temporary memory operative to record diagnostic medical data; and a long-term memory interfacing with the temporary memory and operative to record at least a portion of the diagnostic data stored in the temporary memory; and
    an adaptive-based diagnostic controller operative to control the recording of diagnostic data such that no data is recorded in the temporary memory until the detection of predetermined recording triggers indicative of an impending cardiac arrhythmia, wherein the cardiac arrhythmia indicated as impending, is not currently present, and no data is transferred from the temporary memory and recorded in the long-term memory until it has been determined that a cardiac arrhythmia did actually occur and further operative to adaptively modifying the recording triggers so as to reduce the likelihood of any unnecessary recording of diagnostic data in the temporary memory.

23. A system for adaptively controlling the recording of diagnostic data within an implantable medical device comprising:

an implantable housing having therein, means for temporarily storing data; and means for long-term storage of data stored in the means for temporarily storing data, wherein the means for temporarily storing data interfaces with the means for long-term storage of data;

means for controlling the recording of diagnostic data within the means for temporarily storing data such that no data is stored in the means for temporarily storing data until the detection of predetermined recording triggers indicative of an impending cardiac arrhythmia, wherein the cardiac arrhythmia indicated as impending, is not currently present and no data is transferred from the means for temporarily storing data and recorded in the means for long-term storage of data until it has been determined that a cardiac arrhythmia did actually occur; and means for adaptively modifying the recording triggers so as to reduce the likelihood of any unnecessary recording of diagnostic data in the means for temporarily storing data.

* * * * *